United States Patent [19]
Petersen

[11] Patent Number: 5,672,178
[45] Date of Patent: Sep. 30, 1997

[54] FIXATION PIN

[76] Inventor: Thomas D. Petersen, 9680 Alto Dr., La Mesa, Calif. 91941

[21] Appl. No.: 583,654

[22] Filed: Jan. 5, 1996

[51] Int. Cl.⁶ ..................................... A61B 17/56
[52] U.S. Cl. .......................... 606/75; 606/59; 606/72; 411/451; 411/482
[58] Field of Search ............... 606/75, 72, 67, 606/62, 59; 411/451, 452, 482, 439, 473, 474

[56] References Cited

U.S. PATENT DOCUMENTS

| | | | |
|---|---|---|---|
| 456,723 | 7/1891 | Harvey | 411/452 |
| 2,251,202 | 7/1941 | Purtell | 411/452 |
| 4,430,761 | 2/1984 | Niederer et al. | 606/62 |
| 4,712,541 | 12/1987 | Harder et al. | 606/62 |
| 4,755,091 | 7/1988 | Potucek et al. | 411/452 |
| 4,869,242 | 9/1989 | Galluzzo | 411/482 |
| 5,011,354 | 4/1991 | Brownlee | 411/439 |
| 5,306,275 | 4/1994 | Bryan | 606/72 |

*Primary Examiner*—Michael Buiz
*Assistant Examiner*—Julian W. Woo
*Attorney, Agent, or Firm*—H. Jay Spiegel

[57] ABSTRACT

A fixation pin has a cylindrical body having a proximal end with two axially separated heads with an annular groove between them. The distal end of the cylindrical body has a tapered conical point. In the preferred embodiment, the cylindrical body has a plurality of circumferentially spaced longitudinally extending grooves which extend from just proximal of the pointed end of the fixation pin, proximally toward the proximal end. Each groove extends into the cylindrical body to an extent not exceeding 30% of the diameter of a cross-section of the cylindrical body and each groove has an outwardly facing opening which subtends in the range of about 7% to about 17% of the circumference of the cylindrical body. The grooves receive bone material when the pin is driven into a bone and prevent rotation of the pin while preventing the pin from backing out of the bone.

12 Claims, 1 Drawing Sheet

U.S. Patent    Sep. 30, 1997    5,672,178
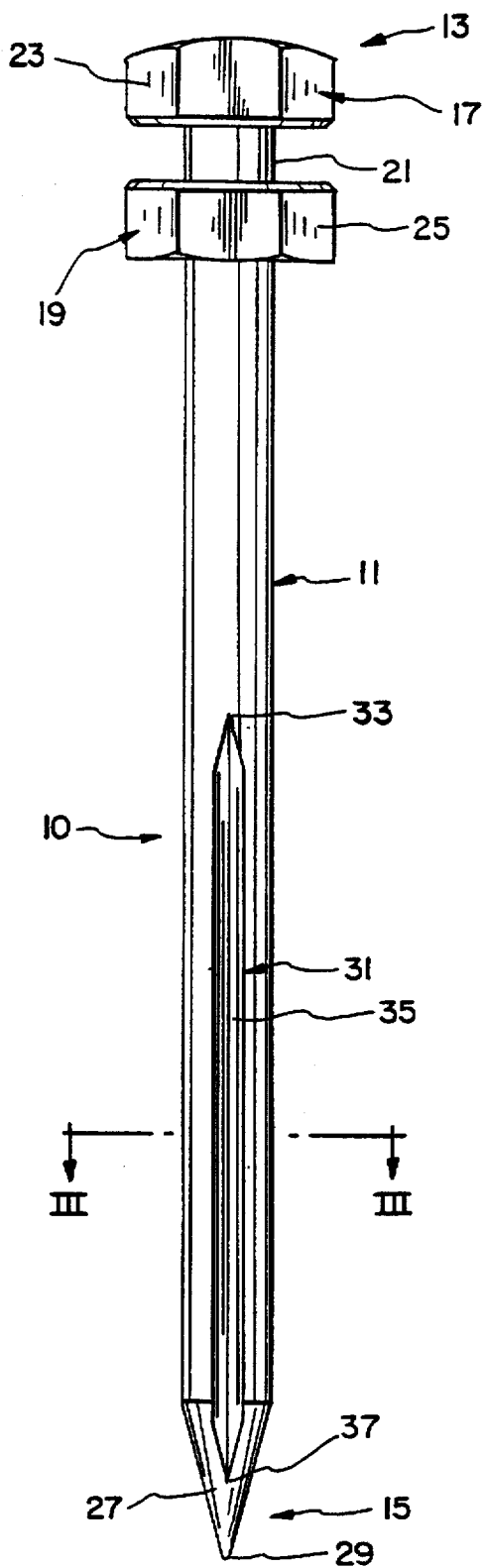
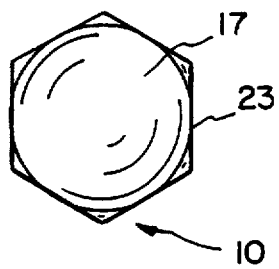
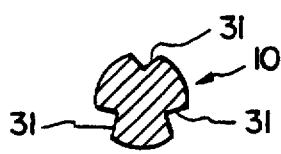

FIXATION PIN

BACKGROUND OF THE INVENTION

The present invention relates to a fixation pin. In the prior art, fixation pins are known and are used, for example, in the performance of total knee prosthetic surgery, to fixate a bone cutting fixture on a location on a bone where resection of the bone using a surgical saw is to take place.

Surgical saws, particularly those of the sagittal type, set up vibrations in the bone due to their oscillations and reciprocations during sawing. Applicant has found that when such vibrations occur, fixation pins tend to begin rotating and thereafter begin to back out of the bone in which they have been driven, resulting in undesirable movements of bone cutting fixtures, thereby resulting in the potential for inaccurate resection of bones in the performance of surgery.

If rotation of fixation pins can be prevented, the subsequent backing out of such fixation pins can be prevented. It is with this goal in mind that the present invention was developed.

The following prior art is known to Applicant:

U.S. Pat. No. 2,557,669 to Lloyd discloses an adapter for a "Smith-Peterson" nail. The nail includes a shaft having three longitudinal and radially extending fins with a sharpened forward edge.

U.S. Pat. No. 3,002,514 to Deyerle discloses a hip setting pin having a cylindrical base portion and three axially elongated fins.

U.S. Pat. No. 3,076,453 to Tronzo discloses a hip nail having an elongated tapered body of generally triangular cross-section.

U.S. Pat. No. 3,433,220 to Zickel discloses an intramedullary rod and cross-nail assembly for treating femur fractures with the cross-nail having a generally cylindrical cross-section interrupted at an inner end portion by longitudinal grooves alternating with fins with the grooves being quite deep and approaching the center of the cross-nail.

U.S. Pat. No. 3,561,437 to Orlich discloses an apparatus for fixing fractures of the femur including a "Smith-Petersen" type nail having a head and a body supporting three flanges which extend substantially the entire length of the nail and are equidistantly spaced apart at angles of 120°.

U.S. Pat. No. 4,103,683 to Neufeld discloses a subtrochanteric nail which is scalloped at a plurality of locations about its circumference with the openings of the scalloped portions taking up a large portion of the circumference thereof.

U.S. Pat. No. 4,712,541 to Harder et al. discloses a bone nail and instruments for the treatment of fractures wherein one embodiment thereof contemplates a cross-section having the shape of a "Maltese cross".

U.S. Pat. No. 4,805,607 to Engelhardt et al. discloses a modular intramedullary nail system including an elongated body having elongated scalloped recesses therein having large openings that subtend a large portion of the circumference thereof.

U.S. Pat. No. 5,053,035 to McLaren discloses a flexible intramedullary fixation rod having a cylindrical body with a multiplicity of fins extending radially outwardly therefrom.

The present invention differs from the teachings of these references as contemplating a fixation pin designed to affix a bone cutting fixture to a bone which includes one or more shallow grooves in a cylindrical body.

SUMMARY OF THE INVENTION

The present invention relates to a fixation pin. The present invention includes the following interrelated objects, aspects and features:

(A) In a first aspect of the present invention, the present invention contemplates a fixation pin intended to be used to releasably attach a bone cutting fixture to a bone structure to facilitate the performance of bone resection while performing surgery such as total knee surgery.

(B) The inventive fixation pin includes an elongated cylindrical body having a proximal end and a distal end. At the distal end of the cylindrical body, a generally conical point is provided. At the proximal end, in the preferred embodiment, a double head structure is provided including a space between the heads comprising an annular groove which is provided to allow the user to insert an instrument within the annular groove to remove the fixation pin from the associated bone.

(C) The elongated body has at least one and preferably three elongated grooves therein. An odd number of grooves equidistantly spaced about the circumference of the cylindrical body is preferred because, in such configuration, each groove will be devoid of a diametrically opposed groove.

(D) In the preferred embodiment, each groove has a major portion of generally V-shaped cross-section with the base of the "V" defining a right angle. In the preferred embodiment, each groove is relatively shallow as compared to the diameter of the cylindrical body, having a maximum depth no greater than 30% of the diameter of the cylindrical body. In the preferred embodiment, the opening of each groove subtends no more than about ⅙ of the circumference of a cross-section of the cylindrical body.

(E) When fixation pins are employed in accordance with the teachings of the present invention, they may be driven into a bone to fixate a bone cutting fixture thereon. Applicant has found that when a saw is engaged on the bone cutting fixture to resect the bone during the performance of surgery, vibrations imparted to the bone cutting fixture by the saw blade do not cause the inventive fixation pin to either rotate or retract. Fixation pins in accordance with the teachings of the present invention are maintained in driven position maintaining, firmly, the position of the bone cutting fixture on the bone to allow accurate resection of the bone to take place.

Accordingly, it is a first object of the present invention to provide a fixation pin.

It is a further object of the present invention to provide such a fixation pin including an elongated cylindrical body having a distal conical point and a proximal double head defining an annular groove.

It is a further object of the present invention to provide such a bone fixation pin with one or more longitudinally elongated shallow grooves designed to prevent fixation pin rotation and retraction.

It is a still further object of the present invention to provide such grooves in an odd number so that no groove has a groove diametrically opposite thereto.

It is a still further object of the present invention to provide such grooves with a V-shaped cross-section.

These and other objects, aspects and features of the present invention will be better understood from the following detailed description of the preferred embodiment when read in conjunction with the appended drawing figures.

BRIEF DESCRIPTION OF THE DRAWINGS

FIG. 1 shows a side elevational view of the present invention.

FIG. 2 shows a top view of the present invention.

FIG. 3 shows a cross-sectional view along the line III—III of FIG. 1.

SPECIFIC DESCRIPTION OF THE PREFERRED EMBODIMENT

With reference to the figures, the present invention is generally designated by the reference numeral 10 and is seen to include an elongated cylindrical body 11 having a proximal end 13 and a distal end 15. At the proximal end 13 of the inventive fixation pin 10, a double head is provided including a proximal head 17 and a more distal head 19 defining an annular groove 21 therebetween. When the inventive pin 10 is driven into a bone (not shown), the proximal head 17 is struck by an instrument such as a hammer (not shown). When it is desired to remove the pin 10 from the bone, an instrument (not shown) is inserted into the groove 21 and a pulling force is imposed thereon to retract the pin 10 from the bone. As best seen in FIG. 2, the proximal head 17 has a periphery 23 that is generally hexagonal in configuration. A similar periphery 25 is provided for the head 19.

At the distal end 15 of the pin 10, a generally conically shaped portion 27 is provided that terminates in a pointed end 29, the purpose for which is self-evident.

Along the cylindrical body 11 and extending into the conically shaped portion 27 are a plurality of circumferentially spaced grooves 31 of which one such groove is shown in FIG. 1. The circumferential spacing of the grooves 31 is seen in FIG. 3. Also shown in FIG. 3 is the V-shaped cross-section of each groove which, in the preferred embodiment, subtends an angle of 90° (a right angle). This angle can range from about 60° to about 120°. Each groove 31 includes a proximal commencement 33 that diverges out to a main portion 35 which then converges within the conical portion 27 to a distal point 37. While the inventive fixation pin 10 is effective employing only a single groove 31, in the preferred embodiment, three such grooves 31 are provided. Furthermore, in order to maintain the structural integrity of the cylindrical body 11 of the pin 10, in the preferred embodiment, an odd number of grooves 31 are provided so that, as clearly understood from FIG. 3, each groove 31 is devoid of a diametrically opposed groove.

As is clearly understood from FIGS. 1 and 3, each groove is relatively shallow as compared to the diameter of the cylindrical portion 11 of the pin 10 and subtends only a small portion of the circumference thereof. In the preferred embodiment of the present invention, each groove has a depth approximately 20% of the diameter of a cross-section of the cylindrical portion 11. In the preferred embodiment, each groove 31 subtends approximately ⅑ of the circumference of a cross-section of the cylindrical body 11 of the pin.

The present invention is intended to encompass grooves having a depth in the range of about 10% to about 30% of the diameter of a cross-section of the cylindrical body 11 of the pin 10 and each such groove having an opening subtending in the range of about 7% to about 17% of the circumference of a cross-section of the cylindrical body 11 of the pin 10. Grooves falling within these ranges of depth and percent circumference of opening define sufficient volumes to permit rotation and retraction prevention in accordance with the teachings of the present invention while not, in any way, affecting the structural integrity of the pin 10.

In the preferred embodiment, the pin is made of any appropriate metal which is inert to human tissues in the surgical site and which may be easily sterilized for re-use. An example of such a material comprises various grades of stainless steel.

As such, an invention has been disclosed in terms of a preferred embodiment thereof which fulfills each and every one of the objects of the invention as set forth hereinabove and provides a new and useful fixation pin of great novelty and utility.

Of course, various changes, modifications and alterations in the teachings of the present invention may be contemplated by those skilled in the art without departing from the intended spirit and scope thereof.

As such, it is intended that the present invention only be limited by the terms of the appended claims.

I claim:

1. A fixation pin for fixating a bone cutting fixture in the performance of orthopaedic surgery, comprising:
   a) an elongated cylindrical body having a proximal end and a distal end;
   b) said proximal end having a head adapted to be struck to drive said pin into a bone;
   c) said distal end converging to a pointed end;
   d) said body having at least one groove therein (1) having a maximum depth in a range of 10% to 30% of a diameter of a cross-section of said body and (2) said groove having an outwardly facing opening subtending from about 7% to about 17% of a circumference of said cross-section whereby, when said pin is driven into a bone, said at least one groove is sized and configured to deter rotation and retraction of said pin.

2. The fixation pin of claim 1, wherein said head comprises a double head including two heads spaced to define an annular groove therebetween.

3. The fixation pin of claim 2, wherein each of said two heads has a hexagonal periphery.

4. The fixation pin of claim 1, wherein said groove has a V-shaped cross-section.

5. The fixation pin of claim 4, wherein said V-shaped cross-section subtends an angle of from about 60° to about 120°.

6. The fixation pin of claim 4, wherein said groove comprises a plurality of grooves equidistantly spaced about said circumference.

7. The fixation pin of claim 6, wherein said plurality of grooves comprises an odd number of grooves.

8. The fixation pin of claim 1, wherein said groove has a proximal end point diverging to a main elongated portion of constant cross-sectional configuration merging with a distal converging portion terminating at a distal end point.

9. The fixation pin of claim 8, wherein said distal end point is within said distal end of said pin.

10. The fixation pin of claim 1, wherein said groove has a maximum depth equal to about 20% of said diameter.

11. The fixation pin of claim 10, wherein said groove opening subtends about one-ninth of said circumference.

12. The fixation pin of claim 1, made of stainless steel.

* * * * *